United States Patent
Pekander

(10) Patent No.: US 10,517,478 B2
(45) Date of Patent: *Dec. 31, 2019

(54) WIRELESS PATIENT MONITORING SYSTEM AND METHOD

(71) Applicant: General Electric Company, Schenectady, NY (US)

(72) Inventor: Otto Valtteri Pekander, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/862,125

(22) Filed: Jan. 4, 2018

(65) Prior Publication Data

US 2018/0153404 A1 Jun. 7, 2018

Related U.S. Application Data

(63) Continuation of application No. 15/041,220, filed on Feb. 11, 2016, now Pat. No. 9,883,800.

(51) Int. Cl.
*A61B 5/00* (2006.01)
*H04Q 9/00* (2006.01)
(Continued)

(52) U.S. Cl.
CPC .......... *A61B 5/0015* (2013.01); *A61B 5/0022* (2013.01); *A61B 5/01* (2013.01);
(Continued)

(58) Field of Classification Search
CPC ........ A61B 5/68; A61B 5/0002; A61B 5/0024
See application file for complete search history.

(56) References Cited

U.S. PATENT DOCUMENTS 5,368,026 A 11/1994 Swedlow et al.
5,743,263 A 4/1998 Baker, Jr.
(Continued)

FOREIGN PATENT DOCUMENTS

EP 2470068 A2 7/2012
EP 2432380 A4 3/2013
(Continued)

OTHER PUBLICATIONS

Pending U.S. Appl. No. 14/586,393, filed Dec. 30, 2014, entitled Common Display Unit for a Plurality of Cableless Medical Sensors:, Muuranto et al.

*Primary Examiner* — Kevin Kim
(74) *Attorney, Agent, or Firm* — Andrus Intellectual Property Law, LLP

(57) ABSTRACT

A method of monitoring a patient includes operating each of one or more wireless sensing devices to measure a physiological parameter from a patient and wirelessly transmit a parameter dataset, and receiving the one or more parameter datasets from the one or more wireless sensing devices. The method further includes calculating a patient condition index based on the one or more parameter datasets, wherein the patient condition index is an indicator of stability of the one or more physiological parameters. A measurement interval is then assigned for each wireless sensing device based on the patient condition index, and each wireless sensing device is operated according to the respective measurement interval.

18 Claims, 8 Drawing Sheets

(51) Int. Cl.

| | |
|---|---|
| *A61B 5/01* | (2006.01) |
| *A61B 5/02* | (2006.01) |
| *A61B 5/0205* | (2006.01) |
| *A61B 5/0408* | (2006.01) |
| *A61B 5/145* | (2006.01) |
| *H04M 9/00* | (2006.01) |
| *G16H 40/67* | (2018.01) |

(52) U.S. Cl.
CPC .............. *A61B 5/02* (2013.01); *A61B 5/0205* (2013.01); *A61B 5/0408* (2013.01); *A61B 5/145* (2013.01); *G16H 40/67* (2018.01); *H04M 9/00* (2013.01); *H04Q 9/00* (2013.01); *H04Q 2209/43* (2013.01)

(56) References Cited

U.S. PATENT DOCUMENTS

| | | |
|---|---|---|
| 5,830,135 A | 11/1998 | Bosque et al. |
| 6,005,658 A | 12/1999 | Kaluza et al. |
| 6,178,343 B1 | 1/2001 | Bindszus et al. |
| 6,594,511 B2 | 7/2003 | Stone et al. |
| 7,803,120 B2 | 9/2010 | Banet et al. |
| 7,993,275 B2 | 8/2011 | Banet et al. |
| 8,180,440 B2 | 5/2012 | McCombie et al. |
| 8,200,321 B2 | 6/2012 | McCombie et al. |
| 8,239,010 B2 | 8/2012 | Banet et al. |
| 8,321,004 B2 | 11/2012 | Moon et al. |
| 8,359,080 B2 | 1/2013 | Diab et al. |
| 8,364,226 B2 | 1/2013 | Diab et al. |
| 8,364,250 B2 | 1/2013 | Moon et al. |
| 8,419,649 B2 | 4/2013 | Banet et al. |
| 8,437,824 B2 | 5/2013 | Moon et al. |
| 8,442,607 B2 | 5/2013 | Banet et al. |
| 8,449,469 B2 | 5/2013 | Banet et al. |
| 8,475,370 B2 | 7/2013 | McCombie et al. |
| 8,506,480 B2 | 8/2013 | Banet et al. |
| 8,527,038 B2 | 9/2013 | Moon et al. |
| 8,545,417 B2 | 10/2013 | Banet et al. |
| 8,554,297 B2 | 10/2013 | Moon et al. |
| 8,570,167 B2 | 10/2013 | Al-Ali |
| 8,571,893 B2 | 10/2013 | Dashefsky et al. |
| 8,574,161 B2 | 11/2013 | Banet et al. |
| 8,591,411 B2 | 11/2013 | Banet et al. |
| 8,594,776 B2 | 11/2013 | McCombie et al. |
| 8,602,997 B2 | 12/2013 | Banet et al. |
| 8,622,922 B2 | 1/2014 | Banet et al. |
| 8,672,854 B2 | 3/2014 | McCombie et al. |
| 8,721,542 B2 | 5/2014 | Al-Ali et al. |
| 8,727,977 B2 | 5/2014 | Banet et al. |
| 8,738,118 B2 | 5/2014 | Moon et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,808,188 B2 | 8/2014 | Banet et al. |
| 8,847,740 B2 | 9/2014 | Kiani et al. |
| 8,852,094 B2 | 10/2014 | Al-Ali et al. |
| 8,888,700 B2 | 11/2014 | Banet et al. |
| 8,909,330 B2 | 12/2014 | McCombie et al. |
| 8,956,293 B2 | 2/2015 | McCombie et al. |
| 8,956,294 B2 | 2/2015 | McCombie et al. |
| 8,979,765 B2 | 3/2015 | Banet et al. |
| 8,989,853 B2 | 3/2015 | Zong |
| 9,028,407 B1 | 5/2015 | Bennett-Guerrero |
| 9,055,928 B2 | 6/2015 | McCombie et al. |
| 9,095,316 B2 | 8/2015 | Welch et al. |
| 9,149,192 B2 | 10/2015 | Banet et al. |
| 9,161,700 B2 | 10/2015 | Banet et al. |
| 9,173,593 B2 | 11/2015 | Banet et al. |
| 9,173,594 B2 | 11/2015 | Banet et al. |
| 9,215,986 B2 | 12/2015 | Banet et al. |
| 2005/0101873 A1 | 5/2005 | Misczynski et al. |
| 2007/0167850 A1 | 7/2007 | Russell et al. |
| 2008/0300471 A1 | 12/2008 | Al-Ali et al. |
| 2009/0171167 A1 | 7/2009 | Baker, Jr. |
| 2009/0275807 A1 | 11/2009 | Sitzman et al. |
| 2010/0063367 A1 | 3/2010 | Friedman et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2011/0080294 A1 | 4/2011 | Tanishima et al. |
| 2011/0190600 A1* | 8/2011 | McKenna ................ A61B 5/01 600/301 |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0288421 A1 | 11/2011 | Banet et al. |
| 2012/0029300 A1 | 2/2012 | Paquet |
| 2012/0108983 A1 | 5/2012 | Banet et al. |
| 2012/0190949 A1 | 7/2012 | McCombie et al. |
| 2013/0109937 A1 | 5/2013 | Banet et al. |
| 2013/0116515 A1 | 5/2013 | Banet et al. |
| 2014/0025010 A1 | 1/2014 | Stroup et al. |
| 2014/0031787 A1 | 1/2014 | Burnes et al. |
| 2014/0081099 A1 | 3/2014 | Banet et al. |
| 2014/0088385 A1 | 3/2014 | Moon et al. |
| 2014/0142445 A1 | 5/2014 | Banet et al. |
| 2014/0163393 A1 | 6/2014 | McCombie et al. |
| 2014/0200415 A1 | 7/2014 | McCombie et al. |
| 2014/0235964 A1 | 8/2014 | Banet et al. |
| 2014/0257056 A1 | 9/2014 | Moon et al. |
| 2014/0275818 A1 | 9/2014 | Kassem et al. |
| 2014/0276145 A1 | 9/2014 | Banet et al. |
| 2014/0276175 A1 | 9/2014 | Banet et al. |
| 2014/0301893 A1 | 10/2014 | Stroup et al. |
| 2015/0042466 A1 | 2/2015 | Kiani et al. |
| 2015/0164437 A1 | 6/2015 | McCombie et al. |
| 2015/0196257 A1 | 7/2015 | Yousefi et al. |
| 2015/0208966 A1 | 7/2015 | Al-Ali |
| 2015/0282717 A1 | 10/2015 | McCombie et al. |
| 2016/0262641 A1 | 9/2016 | Kurzenberger |

FOREIGN PATENT DOCUMENTS

| | | |
|---|---|---|
| EP | 2162059 A4 | 10/2013 |
| EP | 2470067 A4 | 10/2013 |
| EP | 2560550 A4 | 12/2013 |
| EP | 2675346 A1 | 12/2013 |
| EP | 2675348 A1 | 12/2013 |
| EP | 2775917 A2 | 9/2014 |
| EP | 2432378 A4 | 12/2014 |
| EP | 24442709 A4 | 12/2014 |
| EP | 2519144 A4 | 3/2015 |
| EP | 2658440 A4 | 4/2015 |
| EP | 2544584 A4 | 7/2015 |
| EP | 2910182 A2 | 8/2015 |
| WO | 2010135516 A2 | 11/2010 |
| WO | 2010148205 A1 | 12/2010 |
| WO | 2011032132 A2 | 3/2011 |
| WO | 2011032132 A3 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |
| WO | 2010135518 A2 | 11/2011 |
| WO | 2012077113 A2 | 6/2012 |
| WO | 2012092303 A1 | 7/2012 |
| WO | 2012112885 A1 | 8/2012 |
| WO | 2012112891 A1 | 8/2012 |

(56) References Cited

FOREIGN PATENT DOCUMENTS

| | | |
|---|---|---|
| WO | 2013071014 A2 | 5/2013 |
| WO | 2013071014 A3 | 5/2013 |
| WO | 2014015254 A1 | 1/2014 |
| WO | 2014165620 A1 | 10/2014 |
| WO | 2015120330 A1 | 8/2015 |
| WO | 2015173539 A1 | 11/2015 |

* cited by examiner

WIRELESS PATIENT MONITORING SYSTEM AND METHOD

CROSS REFERENCE TO RELATED APPLICATION

This application is a continuation of U.S. patent application Ser. No. 15/041,220, filed Feb. 11, 2016, which is incorporated herein by reference in entirety.

BACKGROUND

The present disclosure relates generally to medical devices and, more specifically, to medical monitoring devices for monitoring a patient's physiology and health status.

In the field of medicine, physicians often desire to monitor multiple physiological characteristics of their patients. Oftentimes, patient monitoring involves the use of several separate monitoring devices simultaneously, such as a pulse oximeter, a blood pressure monitor, a heart monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to a single monitor, resulting in multiple wires running across the patient's body. Thus, currently available patient monitoring devices often inhibit patient movement, requiring a patient to stay in one location or to transport a large monitor with them when they move from one place to another.

Further, currently available monitoring devices are often power intensive and either require being plugged in to a wall outlet or require large battery units that have to be replaced and recharged every few hours. Thus, monitoring multiple patient parameters is power intensive and battery replacement is costly in labor and parts. Thus, frequent monitoring is often avoided in order to limit cost and patient discomfort, and instead patient parameters are infrequently spot checked, such as by periodic nurse visits one or a few times a day. While there are some patients that require continuous, real-time monitoring, such as those patients experiencing a critical health condition, the vast majority of patients need only periodic monitoring to check that their condition has not changed. However, patients that are not being regularly monitored may encounter risky health situations that that go undetected for a period of time, such as where rapid changes occur in physiological parameters that are not checked by a clinician until hours later or until a critical situation occurs.

SUMMARY

The present disclosure generally relates to a patient monitoring system and method.

A method of monitoring a patient includes operating each of one or more wireless sensing devices to measure a physiological parameter from a patient and wirelessly transmit a parameter dataset, and receiving the one or more parameter datasets from the one or more wireless sensing devices. The method further includes calculating a patient condition index based on the one or more parameter datasets, wherein the patient condition index is an indicator of stability of the one or more physiological parameters. A measurement interval is then assigned for each wireless sensing device based on the patient condition index, and each wireless sensing device is operated according to the respective measurement interval.

One embodiment of a patient monitoring system includes one or more wireless sensing devices, each wireless sensing device configured to measure at least one physiological parameter from a patient and wirelessly transmit a parameter dataset. The system further includes a receiver that receives the parameter dataset from the wireless sensing device, a processor, and a monitoring regulation module executable on the processor. The monitoring regulation module is executable to access a minimum measurement interval for each of the one or more wireless sensing devices and process the one or more parameter datasets to calculate a patient condition index, wherein the patient condition index is an indicator of stability of the one or more physiological parameters. The monitoring regulation module is further executable to assign a measurement interval for each of the one or more wireless sensing devices based on the patient condition index, wherein the measurement interval is not less than the minimum measurement interval for the respective wireless sensing device. The monitoring regulation module is further executable to instruct each of the one or more wireless sensing devices to operate at the respective measurement interval.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings:

FIGS. 5-7A and 7B depict various embodiments of a method of monitoring a patient.

DETAILED DESCRIPTION

Figure 1:
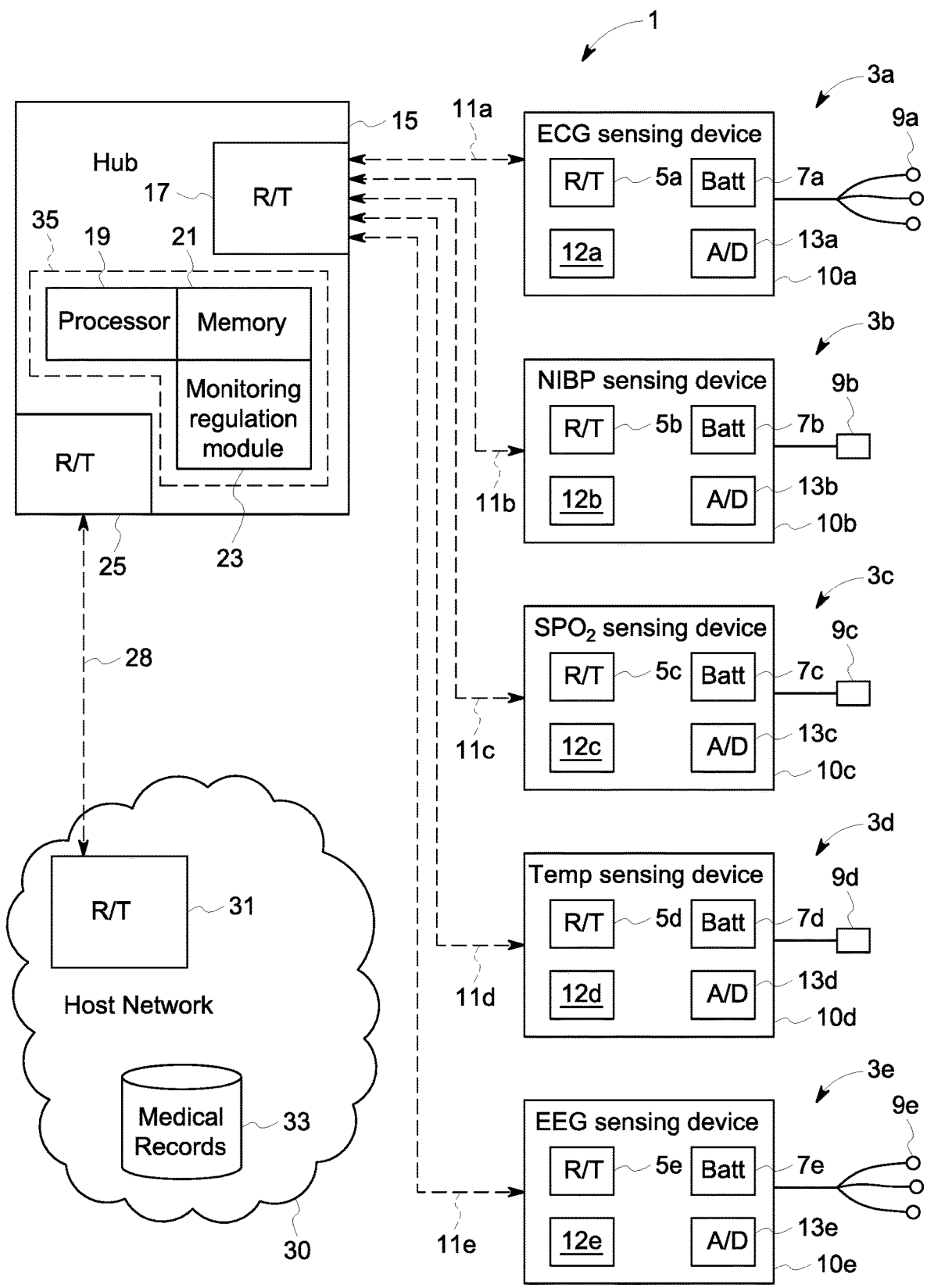
FIG. 1 provides a schematic diagram of one embodiment of a wireless patient monitoring system.

The present inventor has recognized that wireless monitoring systems are desirable for patient comfort, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. In order to do so, the size of the wireless sensing devices must be small. The present inventor has recognized that an important aspect of decreasing the size and weight of wireless sensing devices is decreasing battery size, and that a weakness in the development of wireless sensing devices has been power consumption and requirement for long battery times.

In view of his recognition of problems and challenges in the development of wireless sensing devices, the present inventor developed the disclosed system and method to minimize power consumption of the wireless sensing devices. As provided herein, battery demand for each wireless sensing device, and thus power requirements for the system as a whole, are decreased by selectively and intelligently operating the wireless sensing devices on an infrequent basis when the patient's condition is stable and continuous patient monitoring is unnecessary. In the patient monitoring method and system disclosed herein, one or more wireless sensing devices are controlled to operate at a measurement interval that is determined based on a patient condition index that indicates the stability of one or more physiological parameters measured from the patient by the wireless sensing devices. The measurement interval may be different for each wireless sensing device depending on the type of physiological monitoring performed by that device and the medical needs of the patient. For example, a minimum measurement interval may be set for each wireless sensing device, which may be set based on patient care standards, patient diagnosis, patient medical history, and/or previous monitoring data for the patient. Moreover, the patient condition index may be configured to account for health information specific to the patient, such as a diagnosis or a medical history for the patient (e.g., recent medical procedures performed, medication being administered, or the like). Accordingly, the wireless sensing devices are intelligently controlled to enable maximum continuous patient monitoring capabilities when necessary, but can be operated in a reduced monitoring mode when the patient seems stable in order to reduce the power requirements of the wireless sensing devices and increase the battery life of the devices.

Another benefit of the system and method disclosed herein is that the system automatically determines when the patient condition has deteriorated and automatically initiates continuous monitoring by all wireless sensing devices. Thus, when a clinician responds to an alarm condition, monitoring data is already available and is continuously being updated for all physiological parameters monitored by the system. This is an improvement over prior art systems, where clinicians responding to an alarm condition are required to initiate monitoring by various monitoring or sensing devices and wait for those devices to produce measurements in order to fully assess the patient's condition.

In various embodiments, wireless sensing devices measuring different physiological parameters may be networked to a central hub or primary sensing device that determines the patient condition index and the measurement interval for each of the wireless sensing devices in the network. The hub may communicate with a central, host network, such as of the medical facility. In another embodiment, the wireless sensing devices may communicate with the host network that calculates the patient stability index and assigns the measurement intervals. There, the wireless sensing devices may communicate with the host network directly, or indirectly through the hub. For example the hub may serve as an amplifier and/or router for communication between the wireless sensing devices and the host network.

FIG. 1 depicts one embodiment of a patient monitoring system 1 containing five wireless sensing devices 3a-3e in wireless communication with a hub 15. The hub 15 is in wireless communication with a host network 30 that contains medical records database 33. For example, the hub device 15 may be attached to the patient's body, placed on or near the patient's bed, or positioned within range of the patient, such as in the same room as the patient. The hub device 15 may be a separate, stand alone device, or it may be incorporated and/or housed with another device within the system 1, such as housed with one of the wireless sensing devices 3a-3e. Each wireless sensing device 3a-3e contains one or more sensors 9a-9e for measuring a physiological parameter from a patient, and also includes a base unit 10a-10e that receives the physiological parameter measurements from the sensors 9a-9e and transmits a parameter dataset based on those measurements to the hub device 15 via communication link 11a-11e. The sensors 9a-9e may be connected to the respective base unit 10a-10e by wired or wireless means. The sensors 9a-9e may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like.

In the depicted embodiment, a first wireless sensing device 3a is an ECG sensing device having sensors 9a that are ECG electrodes. A second wireless sensing device 3b is a non-invasive blood pressure (NIBP) sensing device with a sensor 9b that is a blood pressure cuff including pressure sensors. A third wireless sensing device 3c is a peripheral oxygen saturation (SpO2) monitor having sensor 9c that is a pulse oximetry sensor, such as a standard pulse oximetry sensor configured for placement on a patient's fingertip. A fourth wireless sensing device 3d is a temperature monitor having sensor 9d that is a temperature sensor. The depicted embodiment of the system 1 further includes a fifth wireless sensing device 3e that is an EEG monitor having sensors 9e that are EEG electrodes. It should be understood that the patient monitoring system 1 of the present disclosure is not limited to the examples of sensor devices provided, but may be configured and employed to sense and monitor any clinical parameter. The examples provided herein are for the purposes of demonstrating the invention and should not be considered limiting.

The base units 10a-10e of each of the exemplary wireless sensing devices 3a-3e may include analog-to-digital (A/D) converters 13a-13e, which may be any devices or logic sets capable of digitizing analog physiological signals recorded by the associated sensors 9a-9e. For example, the A/D converters 13a-13e may be Analog Front End (AFE) devices. The base units 10a-10e may further include processors 12a-12e that receive the digital physiological data from the A/D converters 13a-13e and create a parameter dataset for transmission to the hub device 15 and for the host network 30. Each base unit 10a-10e may be configured differently depending on the type of wireless sensing device, and may be configured to perform various signal processing functions and or sensor control functions. To provide just a few examples, the processor 12a in the ECG sensing device 3a may be configured to filter the digital signal from the ECG sensors 9a to remove artifact and/or to perform various calculations and determinations based on the recorded cardiac data, such as heart rate, QRS interval, ST-T interval, or the like. The processor 12b in the NIBP monitor 3b may be configured, for example, to process the physiological data recorded by the sensors 9b in a blood pressure cuff to calculate systolic, diastolic, and mean blood pressure values for the patient. The processor 12c of the SpO2 sensing device 3c may be configured to determine a blood oxygenation value for the patient based on the digitized signal received from the pulse oximetry sensor 9c. The processor 12d of the temperature sensing device 3d may be configured to, for example, determine a temperature for the patient, such as a mean temperature based on the digitized temperature data received from the thermal sensor 9d. And the processor 12e of the EEG sensing device 3e may be configured, for example, to determine a depth of anesthesia measurement value, such as an entropy value or a sedation responsiveness index value.

Accordingly, the processor 12a-12e may develop a datasets that, in addition to the recorded physiological data, also include values measured and/or calculated from the recorded physiological data. The respective processors 12a-12e may then control a receiver/transmitter 5a-5e in the relevant wireless sensing device 3a-3e to transmit parameter datasets to the hub device 15 via communication link 11a-11e. The parameter dataset transmitted from the respective wireless sensing devices 3a-3e may include the raw digitized physiological data, filtered digitized physiological data, and/or processed data indicating information about the respective physiological parameter measured from the patient.

In other embodiments, the processors 12a-12e may not perform any signal processing tasks and may simply be configured to perform necessary control functions for the respective wireless sensing device 3a-3e. In such an embodiment, the parameter data set transmitted by the respective processor 12a-12e may simply be the digitized raw data or digitized filter data from the various sensor devices 9a-9e.

Each wireless sensing device 3a-3e includes a battery 7a-7e that stores energy and powers the various aspects of the wireless monitor. Each processor 12a-12e may further include power management capabilities, especially where the respective wireless sensing device 3a-3e contains more demanding electromechanical aspects. Each processor 12a-12e may monitor a battery status 43a-43e (FIG. 3), such as a charge level of the relevant battery 7a-7e. The processor 12a-12e may communicate the battery status to the hub device 15 by the communication link 11a-11e. Alternatively or additionally, the processor 12a-12e may control a local display on the wireless sensing device 3a-3e to display the battery status 43a-43e, and/or may control the emission of an audio and/or visual alert regarding the battery status 43a-43e.

The receiver/transmitter 5a-5e of each wireless sensing device 3a-3e communicates via the respective communication link 11a-11e with the receiver/transmitter 17 of the hub device 15, which may include separate receiving and transmitting devices or may include an integrated device providing both functions, such as a transceiver. The receiver/transmitters 5a-5e of the wireless sensing devices 3a-3e and the receiver/transmitter 17 of the hub device 15 may be any radio frequency devices known in the art for wirelessly transmitting data between two points. In one embodiment, the receiver/transmitters 5a-5e and 17 may be body area network (BAN) devices, such as medical body area network (MBAN) devices, that operate as a wireless network. For example, the wireless sensing devices 3a-3e may be wearable or portable computing devices in communication with a hub device 15 positioned in proximity of the patient. Other examples of radio protocols that could be used for this purpose include, but are not limited to, Bluetooth, Bluetooth Low Energy (BLE), ANT, and ZIGBEE.

The hub device may further include computing system 35 having processor 19 and memory 21. The hub device 15 may serve to control the wireless sensing devices 3a-3e, and thus may transmit operation commands 45a-45e (FIG. 3) to the respective wireless sensing devices 3a-3e via the communication link 11a-11e to control their monitoring operations. The hub 15 may contain a monitoring regulation module 23 that is a set of software instructions stored in memory and executable on the processor to assess the physiological data collected by the wireless sensing devices 3a-3e and determine a patient condition therefrom, and to control the respective wireless sensing devices 3a-3e according to the patient condition.

For example, the monitoring regulation module 23 may process the one or more parameter datasets 41a-41e (FIG. 3) received from the wireless sensing devices 3a-3e to calculate a patient condition index that is an indicator of stability of the one or more physiological parameters. The patient condition index may be any value that indicates a value of physiological stability for the patient—i.e. indicating whether the monitored physiological parameters being monitored are in a normal range for the patient and remain unchanged for a period of time (stable). For example, the patient condition index may be a value on a linear scale between stable and critical, such as a scale between 1 and 10, where 1 represents that all monitored parameters are in a normal range for the patient and have been in the normal range for at least a predetermined amount of time, and 10 represents a critically unstable, life-threatening emergency that requires immediate intervention by a clinician. In an alternative embodiment, the patient condition index may be a color gradient scale between green, indicating a stable condition, and red, indicating a critically unstable condition. In still other embodiments, the patient condition index may be any series of values capable of being used by the software algorithm to represent the patient condition as an indicator of stability of one or more of the physiological parameters being measured by the wireless sensing devices 3a-3e. As described in further detail herein, the patient condition index may be calculated based equally on all monitored parameters, or may be based more heavily on some subset of the monitored parameters.

The monitoring regulation module 23 then assigns a measurement interval for each wireless sensing device based on the patient condition index and instructs operation of each wireless sensing device 3a-3e according to the respective measurement interval. For example, a minimum measurement interval may be stored for each wireless sensing device 3a-3e and the monitoring regulation module 23 may instruct operation of each wireless sensing device 3a-3e at its minimum measurement interval if the patient condition index indicates that all physiological parameters being measured from the patient are stable. If the patient condition index indicates that the patient condition is unstable, the monitoring regulation module 23 may instruct one or more of the wireless sensing devices 3a-3e to increase the monitoring frequency above the minimum measurement interval as appropriate based on the degree of instability indicated by the patient condition index. For example, the monitoring regulation module 23 may increase the measurement interval proportionally to the level of the patient condition index, and may instruct any level of monitoring between the minimum measurement interval for each wireless sensing device and continuous monitoring for each sensing device depending on the patient condition index. For example, if the patient condition index indicates that the physiological parameters measured from the patient are unstable and that the patient has a critical health condition, then the monitoring regulation module 23 may instruct continuous monitoring operation of all of the wireless sensing devices 3a-3e.

The hub device 15 may communicate with a host network 30 via a wireless communication link 28, such as to transmit the parameter datasets for the respective wireless sensing devices 3a-3e for storage in the patient's medical record. The hub 15 has receiver/transmitter 25 that communicates with a receiver/transmitter 31 associated with the host network 30 on communication link 28, which may operate according to a network protocol appropriate for longer-range wireless transmissions, such as on the wireless medical telemetry service (WMTS) spectrum or on a Wi-Fi-compliant wireless local area network (LAN). The host network 30 may be, for example, a local computer network having servers housed within a medical facility treating the patient, or it may be a cloud-based system hosted by a cloud computing provider. The host network 30 may include a medical records database 33 housing the medical records for the patient, which may be updated to store the parameter datasets recorded and transmitted by the various wireless sensing devices 3a-3e. The host network 30 may further include other patient care databases, such as for monitoring, assessing, and storing particular patient monitoring data. For example, the host network may include an ECG database, such as the MUSE ECG management system produced by General Electric Company of Schenectady, N.Y.

In various embodiments, the hub device 15 may contain software for processing the physiological signals recorded by the various wireless sensing devices 3a-3e. For example, in one embodiment the individual wireless sensing device 3a-3e may perform minimal or no signal processing on the physiological data measured from the patient, and may simply transmit the digitized physiological data recorded from the respective sensors 9a-9e. Software stored in the hub device 15 may then be executed on the processor 19 to calculate various useful parameters from the physiological data, as is explained above with respect to the exemplary wireless sensing devices 3a-3d depicted in FIG. 1. In still other embodiments, minimal or no signal processing may be performed in the hub device 15, and the hub 15 may simply serve to relay the parameter datasets from the wireless sensing devices 3a-3e to the host network 30. In such an embodiment, the computing system 35, including the monitoring regulation module 23, may reside in the host network 30, as is depicted in the embodiment of FIG. 2.

Figure 2:
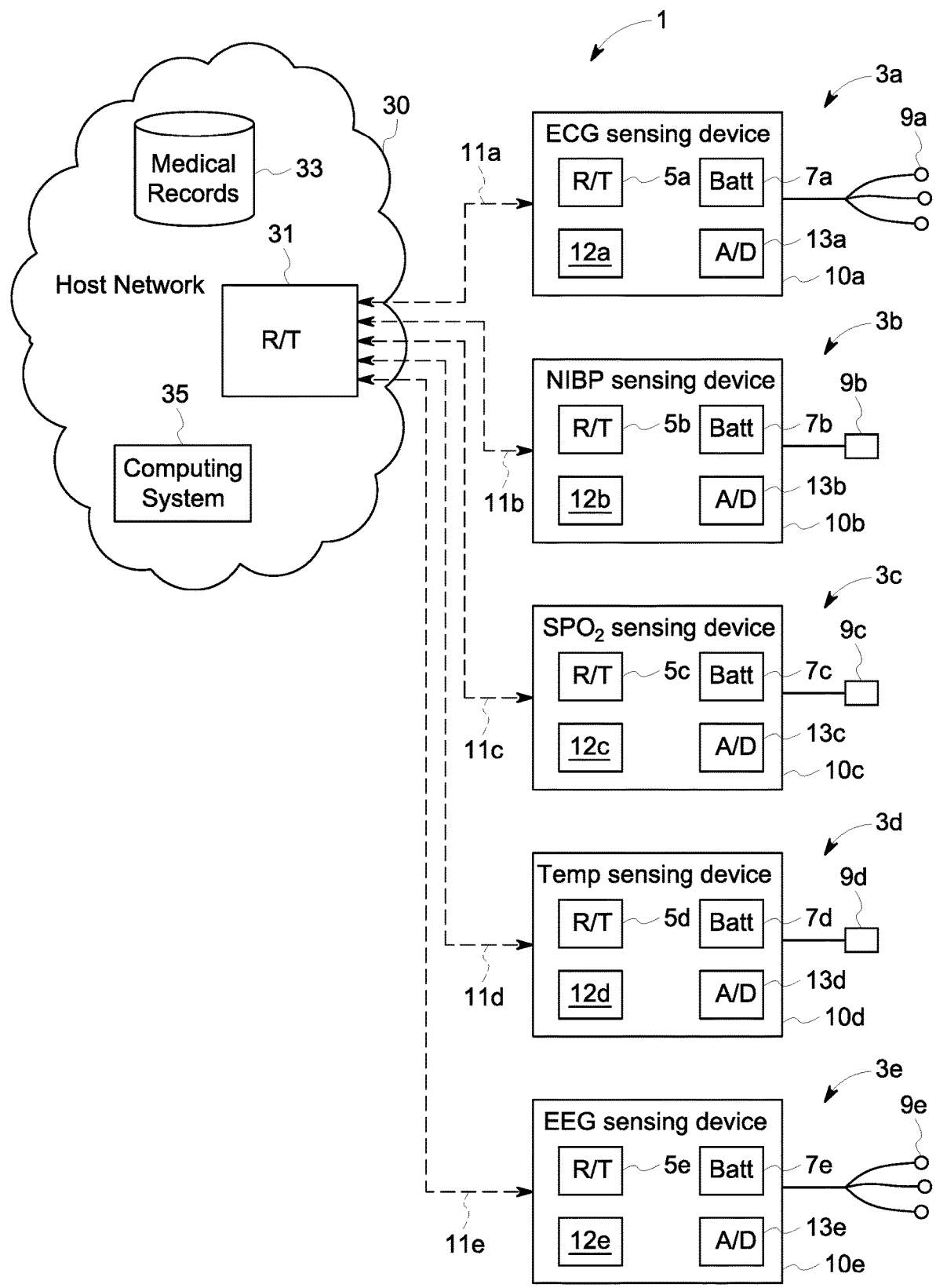
FIG. 2 depicts another embodiment of a wireless patient monitoring system.

In the embodiment of FIG. 2, the hub device 15 is omitted and the wireless sensing devices 3a-3e communicate directly with the host network 30. Thus, the receiver/transmitter 5a-5e of each wireless sensing device 3a-3e may communicate with a receiver/transmitter 31 associated with the host network 30 by the respective communication link 11a-11e. The communication link 11a-11e in this embodiment may operate according to any wireless communication protocol listed above. It may be desirable to operate the communication according to a wireless communication protocol that is appropriate for longer-range transmission. For example, the wireless sensing devices 3a-3e may communicate with the host network 30 on the WMTS spectrum or on the Wi-Fi spectrum. In such an embodiment, receiver/transmitters 31 may be provided throughout a patient care facility, such as a hospital, as needed based on the system configuration and the location of patients being monitored by wireless sensor devices. The host network 30 may house the computing system 35 containing the monitoring regulation module 23, and thus the calculation of the patient condition index and measurement interval assignment may be conducted by the computing system 35 housed in the host network 30. Further, the host network 30 may provide one or more central monitoring stations, such as user interfaces at central locations for attending clinicians to monitor patient conditions and/or receive alarm notifications.

Figure 3:
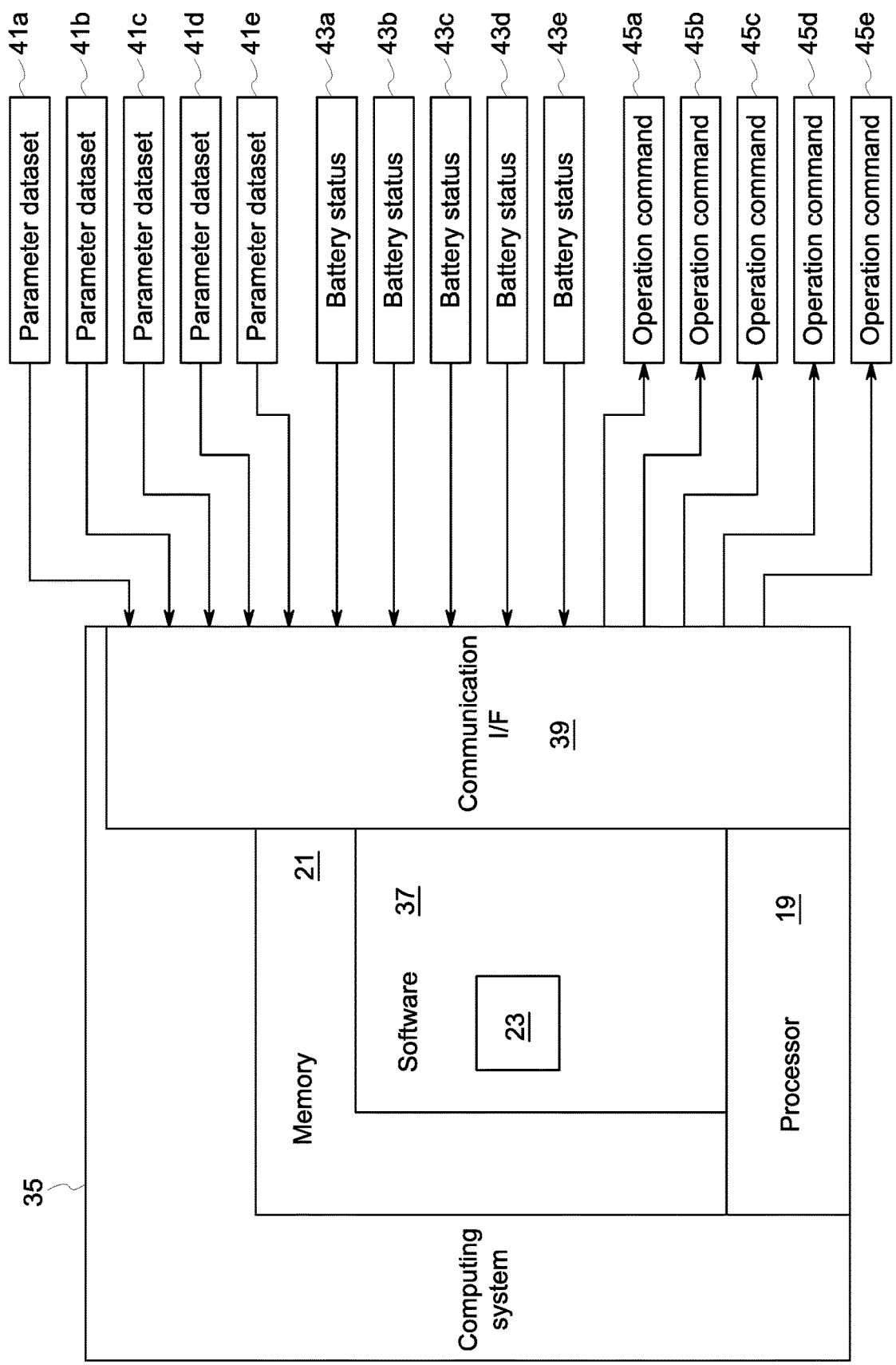
FIG. 3 depicts one embodiment of a computing system portion of a wireless patient monitoring system of the present disclosure.

FIG. 3 provides a system diagram of an exemplary embodiment of the computing system 35 having a monitoring regulation module 23 executable to control the wireless sensing devices 3a-3e. The computing system 35 includes a processor 19, memory 21, software 37, and communication interface 39. The processor 19 loads and executes software 37 from memory 21, including the monitoring regulation module 23, which is an application within the software 37. Each monitoring regulation module 23 includes computer-readable instructions that, when executed by the computing system 35 (including the processor 19), direct the operation as described in detail herein, including to calculate the patient condition index and assign the measurement intervals for the wireless sensing devices 3a-3e.

Although the computing system 35 as depicted in FIG. 3 includes one software element 37 encapsulating one monitoring regulation module 23, it should be understood that one or more software elements having one or more modules may provide the same operation. Similarly, while the description provided herein refers to a single computing system 35 having a single processor 19, it is to be recognized that implementations of such systems can be performed using one or more processors, which may be communicatively connected, and such implementations are considered to be within the scope of the description. Likewise, the computing system 35 may be implemented as several computing systems networked together, including in a cloud computing environment. Such an embodiment may be utilized, for example, where the computing system 35 is part of the host network 30.

The memory 21, which includes the medical record database 33, can comprise any storage media, or group of storage media, readable by processor 19 and/or capable of storing software 37. The memory 21 can include volatile and non-volatile, removable and non-removable storage media implemented in any method or technology for storage of information, such as computer-readable instructions, data structures, program modules, or other data. Memory 21 can be implemented as a single storage device but may also be implemented across multiple storage devices or sub-systems. For example, the software 37 may be stored on a separate storage device than the medical record database 33. Further, in some embodiments the memory 21 may also store the medical record database 33, which could also be distributed, and/or implemented across one or more storage media or group of storage medias accessible within the host network 30. Similarly, medical record database 33 may encompass multiple different sub-databases at different storage locations and/or containing different information which may be stored in different formats.

Examples of memory devices, or storage media, include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processor 19, or may be distributed in one or more servers, which may be at multiple locations and networked, such as in cloud computing applications and systems. In some implementations, the store media can be a non-transitory storage media. In some implementations, at least a portion of the storage media may be transitory. Memory 21 may further include additional elements, such a controller capable, of communicating with the processor 19.

The communication interface 39 is configured to provide communication between the processor 19 and the various other aspects of the system 1, including the wireless sensing devices 3a-3e to receive the parameter datasets 41a-41e and the battery status 43a-43e of each respective device 3a-3e and to transmit the operation command 45a-45e to each respective device 3a-3e. For example, the communication interface 39 may include the receiver/transmitters 17 and 25, and/or the receiver/transmitter 31 described above with respect to the various depicted embodiments.

Figure 4:
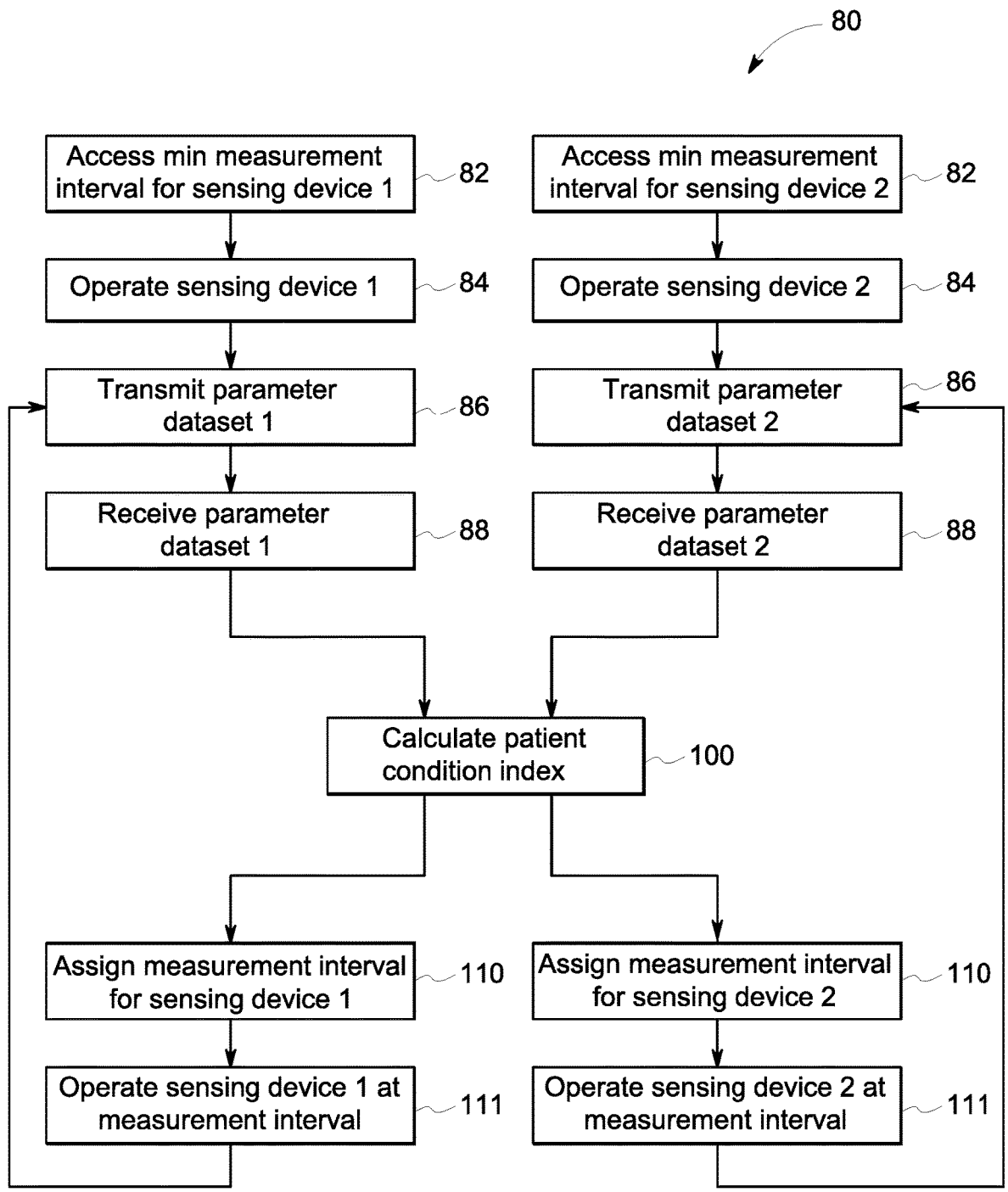
FIG. 4 depicts one embodiment of a method of monitoring a patient.

FIG. 4 depicts one embodiment of a method 80 of monitoring a patient. At step 82, a minimum measurement interval is accessed for each of the wireless sensing devices in the system, which in the embodiment depicted in FIG. 4 includes a first monitor and a second monitor. For example, the monitoring regulation module 23 may access a lookup table or database of minimum measurement intervals stored in memory 21 for each wireless sensing device in the system 1. Alternatively, the minimum measurement interval may be provided to the system by a clinician, such as upon system set up. For example the minimum measurement interval may be a setting established when each wireless sensor device 3a-3n (representing any number of wireless sensing devices) is connected to the system 1. Each of the wireless sensor devices 3a-3n is then operated at step 84 to measure a physiological parameter from the patient, and then to transmit a parameter dataset at step 86. Each of the parameter data sets is received at step 88, such as by the monitoring regulation module 23.

The monitoring regulation module 23 may further be executed on the processor 19 to calculate the patient condition index at step 100. The patient condition index may be based equally on all parameter datasets received at step 88. Alternatively, the patient condition index calculation may weight one or more of the parameter datasets higher than the others. For example, higher weight may be assigned to one or more key parameter datasets based on at least one of a diagnosis of the patient, a medical history of the patient, and/or previous parameter datasets for the patient. For example, the monitoring regulation module 23 may receive input from a clinician instructing a key parameter or providing diagnosis or medical history information that indicates that certain physiological parameters are especially important. In still another embodiment, the monitoring regulation module 23 may access the patient's medical records in the medical records database 33 to identify whether assignment of key parameters is warranted. To provide one example, for a patient recovering from a cardiac procedure, ECG may be identified as a key parameter. Accordingly, the ECG parameter dataset may be weighed more heavily in the patient condition index than the other datasets. In other words, the patient condition index will be more sensitive to changes in the ECG dataset than in the other datasets. Furthermore, the patient condition index may also account for previous parameter datasets and/or previous patient condition indexes. For example, the patient condition index may be sensitive to and reflect abnormal volatility within the parameter datasets, even if the changes remain within the "stable" range. Likewise, if a certain one or more of the parameter datasets has an established history of being very stable, changes in that parameter dataset may be weighted more heavily.

The monitoring regulation module 23 may further be executed on the processor 19 to assign a measurement interval for each monitor at step 110 based on the patient condition index. For example, the monitoring regulation module 23 may access a lookup table that provides the appropriate measurement interval for the associated wireless sensing device based on the patient condition index. In another embodiment, the measurement interval for each monitor may be calculated based on a formula that incorporates the patient condition index. For example, the formula may also account for other factors, such as previous patient condition index values, previous parameter datasets, etc. At step 111, each of the monitors is operated according to the respective measurement interval. In certain embodiments, the wireless sensing devices may be powered down, or turned off, between measurement operations in order to save battery.

Figure 5:
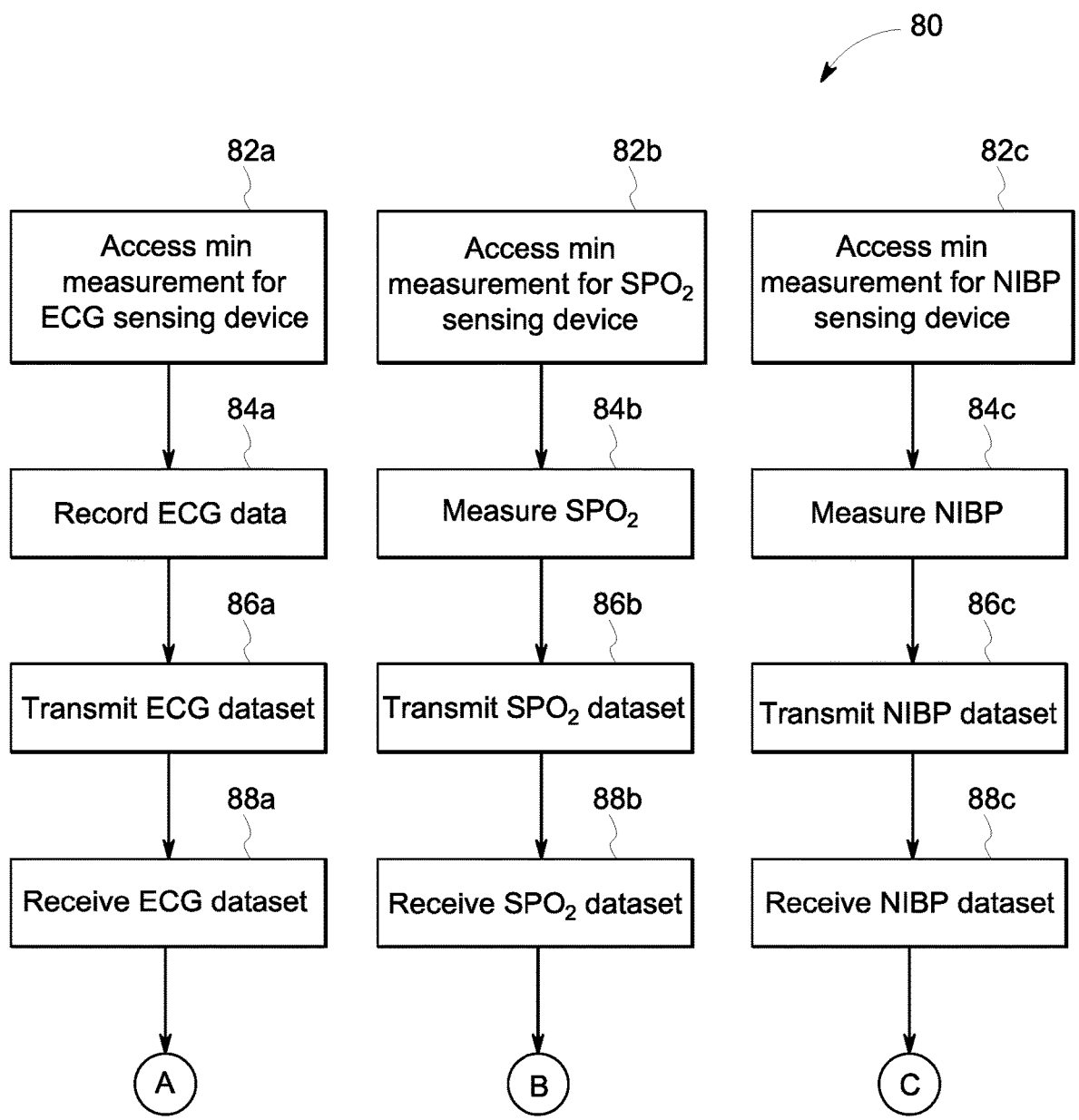

FIGS. 5-7A and 7B depict other embodiments of the method 80 of monitoring a patient. In FIG. 5, steps 82-88 are executed for each of an ECG monitor, an SpO2 monitor, and an NIBP monitor incorporated in the system 1. For the ECG monitor, a minimum measurement interval is accessed for the ECG monitor at step 82a, and for the SpO2 monitor at step 82b, and for the NIBP monitor at step 82c. In embodiments containing other wireless sensing devices, the steps described herein are also executed for those monitors. Meanwhile, each respective wireless sensing device measures a respective physiological parameter and transmits a dataset. The wireless ECG sensing device records ECG data at step 84a and transmits the ECG dataset at step 86a. The ECG dataset is received at step 88a, such as at the hub device 15 or host network 30 containing monitoring regulation module 23. Likewise, the wireless SpO2 sensing device measures SpO2 at step 84b and transmits an SpO2 dataset at step 86b, which is received at step 88b. The wireless NIBP sensing device measures NIBP from the patient at step 84c, and transmits an NIBP dataset at step 86c, which is received at step 88c. The patient condition index is then calculated and the measurement interval assigned, which may be executed by various specific method steps exemplified in FIGS. 6 and 7A-7B.

Figure 6:
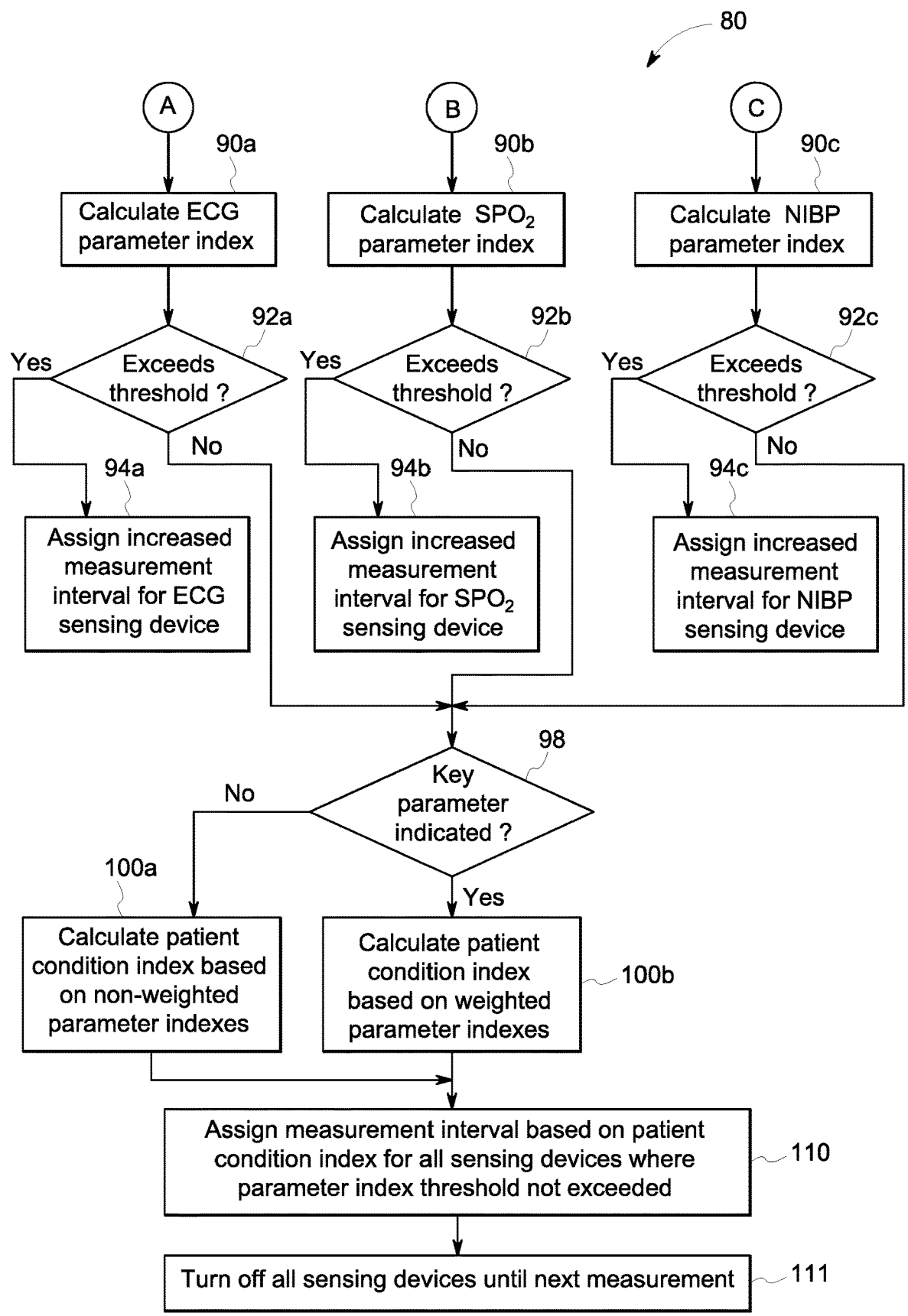

In the embodiment of FIG. 6, a parameter index is calculated based on the parameter dataset from each of the wireless sensing devices. The patient condition index is then calculated based on the various parameter indexes. At step 90a, an ECG parameter index is calculated based on the ECG parameter dataset received at step 88a. For example, the ECG parameter index may reflect whether the values in the ECG dataset are in the normal range and are stable, such as based on previous ECG datasets for that patient or based on population normal values. At step 92a, it is determined whether the ECG parameter index exceeds a threshold indicating that the ECG parameter index is not within the stable range. If the threshold is exceeded, then an increased measurement interval may be assigned for the ECG monitor at step 94a. At step 90b, an SpO2 parameter index is calculated based on the SpO2 dataset received at step 88b. The system determines at step 92b whether a threshold for the SpO2 parameter index is exceeded. If so, then an increased measurement interval is assigned for the SpO2 monitor at step 94b. At step 90c, an NIBP parameter index is calculated based on the NIBP dataset received at step 88c. If the NIBP parameter index exceeds a threshold for that index, which is determined at step 92c, then an increased measurement interval is assigned for the NIBP monitor at step 94c. In various embodiments, the increased measurement interval may reflect the value of the parameter index, such that if the parameter index indicates that the relevant physiological parameter is at a critical level, then continuous monitoring may be assigned for that parameter. The increased measurement interval assigned may be proportional to the amount that the relevant threshold is exceeded. For example, if all of the parameter indexes indicate that the respective physiological parameters are in a critical range, continuous monitoring may be assigned for each and every wireless sensing device accordingly.

For those wireless sensing devices where the relevant parameter index does not exceed the threshold, a measurement interval still needs to be determined, and it is determined based on the patient condition index. In the embodiment depicted in FIG. 6, it is determined at step 98 whether a key parameter is indicated. In other words, the system determines whether to calculate the patient condition index based equally on all of the parameter indexes, or whether certain of the parameter indexes should be weighted more heavily. Such decision may be based on, for example, a diagnosis or medical history for the patient, such as whether the patient is experiencing a medical condition that is likely to manifest in certain ones of the monitored physiological parameters first or to a greater degree than others. If a key parameter is indicated, then the patient condition index is calculated at step 100b based on a formula that weights the key parameter more heavily. For example, a set of formulas for calculation of the patient condition index may be stored in the memory 21 of the computing system 35 and may be accessible to the monitoring regulation module, which may determine and access the appropriate formula. If a key parameter is not indicated at step 98, then the patient condition index is calculated at step 100a based equally on the parameter indexes.

The measurement interval is then calculated at step 110 based on the patient condition index. Specifically, the measurement interval is calculated for each of the wireless sensing devices for which the parameter index threshold was not exceeded at step 92. The wireless sensing devices are then operated according to each of their respective measurement intervals. For example, wireless sensing devices with measurement intervals that are sufficiently long may be turned off at step 111, and then may be reactivated at the end of the interval in order to measure the physiological parameter at the prescribed time. For example, the monitoring regulation module 23 may send a signal to activate each respective wireless sensing device at the prescribed measurement interval. In other embodiments, the monitoring regulation module 23 may provide an instruction of the measurement interval to each respective wireless sensing device, which may then each regulate themselves to measure at that monitoring interval until instructed otherwise.

Figure 7A:
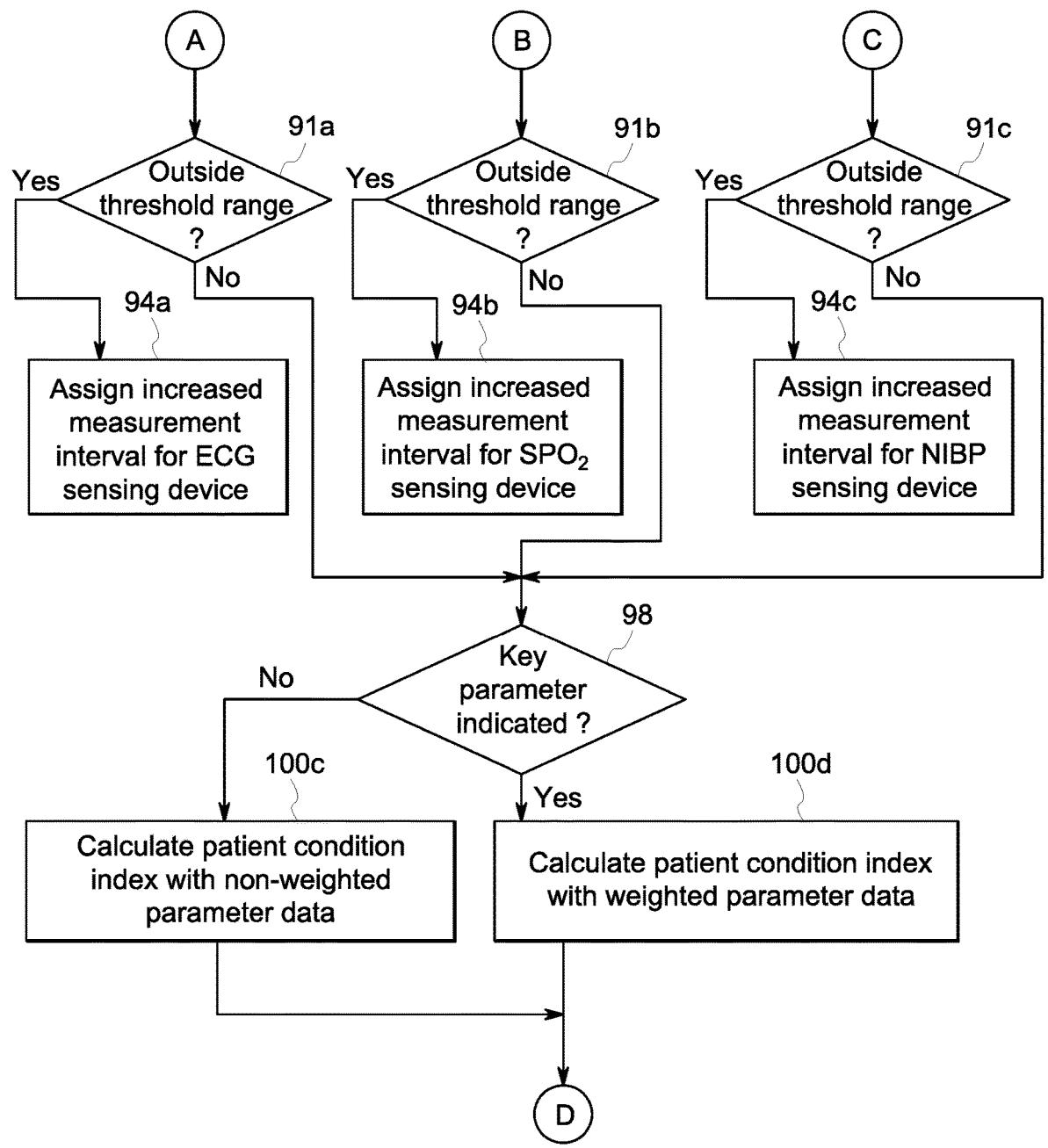
Figure 7B:
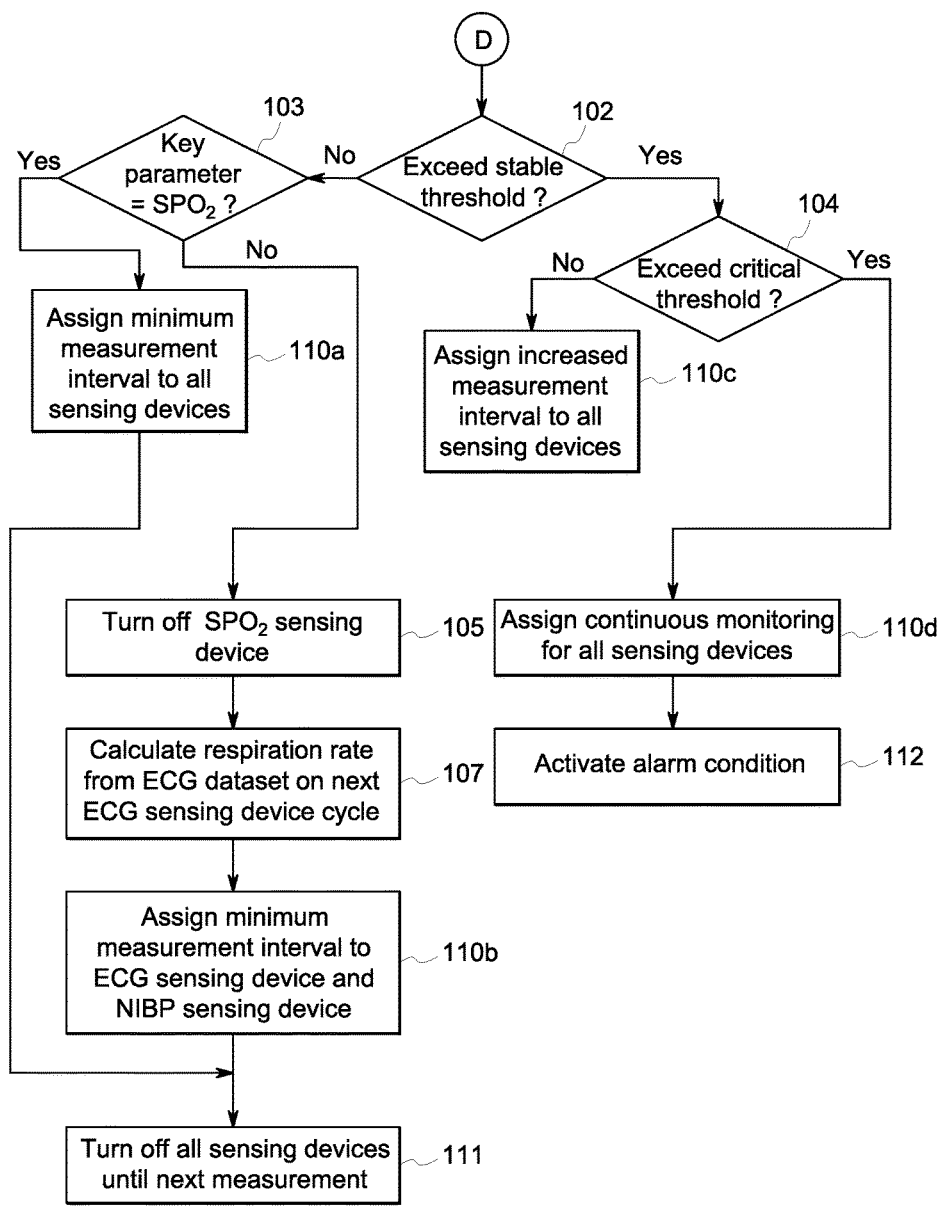

FIGS. 7A-7B depict another embodiment of a method of monitoring a patient. There, the system checks at step 91 whether the values of the relevant parameter dataset are within a threshold range for that type of parameter. The threshold may be set according to any method known in the art for assessing patient monitoring data, and may be a patient-specific threshold range developed based on prior parameter datasets recorded from the patient, or may be a population normal threshold range developed based on a population set relevant to the patient's demographic. In the specific example, step 91a is executed to determine whether the ECG dataset received at step 88a contains values that are outside a threshold range for ECG data. If the ECG dataset is outside of the threshold range, then an increased measurement interval is assigned at step 94a, as is explained above. Likewise, step 91b is executed to determine whether the SpO2 dataset received at step 88b is outside of a threshold range for SpO2 data. If so, then an increased measurement interval is assigned for the SpO2 monitor at step 94b. Likewise, at step 91c it is determined whether the values in the NIBP dataset received at step 88c are outside a threshold range for NIBP data. If so, then an increased measurement interval is assigned at step 94c for the NIBP monitor. As explained above, the increased interval may be proportional to the amount that the relevant data in the dataset exceeds the relevant threshold range, and continuous monitoring may be assigned if the relevant dataset is in a critical range. It should be noted that other embodiments of the method 80 may not execute steps that determine the measurement intervals separately for the wireless sensing devices based on the parameter data from that device, and instead all measurement intervals for the wireless sensing devices may be determined and assigned based on the patient condition index.

Assuming that one or more of the datasets received at step 88 are not outside of a threshold range, step 98 is executed to determine whether a key parameter is indicated. If a key parameter is not indicated, then the patient condition index may be calculated based on all of the received parameter datasets, with each dataset being weighted equally. Alternatively, the patient condition index may be calculated at step 100d based on any formula stored within the system which may weight key parameter datasets more heavily than others.

Turning to FIG. 7B, once the patient condition index is calculated, step 102 is executed to determine whether the patient condition index exceeds a certain threshold indicating stability. If the patient condition index indicates that the patient condition is stable, then certain steps may be executed to minimize battery usage as much as possible. For example, the system may determine whether certain wireless sensing devices may be turned off for an extended period of time, or turned off until the patient condition worsens or the parameter datasets otherwise indicate that the eliminated parameter should be resumed. In such an embodiment, certain physiological parameters no longer being monitored may be estimated based on secondary indicia measured from other parameters measured by other sensing devices. The method depicted in FIGS. 7A-7B provides one such example. Step 103 determines whether SpO2 is a key parameter, and if not, turns off the SpO2 monitor at step 105. The respiration rate will then be calculated from the ECG dataset in the next monitoring cycle, as is indicated by step 107. For example, amplitude modulation of the ECG signal may be used in order to determine respiration rate, a secondary indicia of SpO2, from the ECG dataset. Thus, the SpO2 monitor may be turned off completely, which conserves the battery of the SpO2 monitor, meaning that one less battery will need to be monitored and replaced by clinicians. Further, in certain embodiments, this may also reduce the load on the hub 15 by eliminating the demand on the hub to receive the SpO2 dataset from the SpO2 monitor and transmit that dataset to the host network 30.

In other embodiments of the method 80, alternative or additional power conservation steps may be taken when the patient condition index indicates patient stability. For example, one or more of the wireless sensor devices may modify their operation to a low power mode, such as by transmitting a lesser amount of parameter data at a lesser frequency. As another example, the wireless sensor devices may modify their sensing operation to one that demands less energy. For instance, the wireless ECG sensing device may reduce the number of leads it measures from, such as by reducing from a 12 lead operation to a 5 lead operation or a 3 lead operation.

The minimum measurement interval may then be assigned to the ECG monitor and the NIBP monitor at step 110b, and at step 111 all of the monitors may be turned off until such time as the next measurement is demanded. Returning to step 103, if SpO2 is a key parameter, then the SpO2 monitor will not be turned off, and instead the minimum measurement interval will be assigned to all of the wireless sensing devices.

Such power saving measures exemplified by steps 103-107 would only be executed if the patient is stable. If, on the other hand, the patient condition index indicates at step 102 that a stability threshold is exceeded and thus the patient condition cannot be considered stable, then increased measurement intervals will be assigned accordingly. For example, step 104 may be executed to determine how far the patient condition index is outside of the stable range, such as whether the patient condition index exceeds a critical threshold. If the critical threshold is exceeded, then continuous monitoring may be assigned for all monitors at step 110d and alarms may be activated at step 112 to alert clinicians to the critical patient condition. If the patient condition index indicates some instability, but not a critical condition warranting an alarm, relative increased measurement intervals may be assigned for the wireless sensing devices so that the patient's condition can be monitored appropriately.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A patient monitoring system comprising:
    a first wireless sensing device configured to measure at least a first physiological parameter from a patient and wirelessly transmit a first parameter dataset based on the first physiological parameter measurements;
    a second wireless sensing device configured to measure at least a second physiological parameter from a patient and wirelessly transmit a second parameter dataset based on the second physiological parameter measurements, wherein the second physiological parameter is a different physiological parameter than the first physiological parameter;
    a receiver that receives the first parameter dataset and the second parameter dataset;
    a processor;
    a monitoring regulation module executable on the processor to:
        calculate a patient condition index based on the first parameter dataset and the second parameter dataset, wherein a higher weight is assigned to one of the first parameter dataset or the second parameter dataset, and wherein the patient condition index is an indicator of stability of the first physiological parameter and the second physiological parameter;
        assign a first measurement interval for the first physiological parameter and a second measurement interval for the second physiological parameter based on the patient condition index; and
        operate at least the first wireless sensing device to measure the first physiological parameter at the first measurement interval.

2. The patient monitoring system of claim 1, wherein the monitoring regulation module is further executable on the processor to operate the second wireless sensing device to measure the second physiological parameter at the second measurement interval, wherein the second measurement interval is different than the first measurement interval.

3. The patient monitoring system of claim 1, wherein the monitoring regulation module is further executable on the processor to determine that the patient is stable based on the patient condition index, power down the second wireless sensing device, and then determine a secondary indicia of the second physiological parameter based on the first parameter dataset instead of operating the second wireless sensing device at the second measurement interval.

4. The patient monitoring system of claim 1, wherein the monitoring regulation module is further executable on the processor to select a key parameter based on input from a clinician identifying one of the first physiological parameter and the second physiological parameter as a key parameter, and then to calculate the patient condition index by assigning the higher weight to the key parameter.

5. The patient monitoring system of claim 1, wherein the monitoring regulation module is further executable on the processor to select a key parameter based on a diagnosis, a medical history, at least one and/or previous parameter dataset for the patient, and then to calculate the patient condition index by assigning the higher weight to the key parameter.

6. The patient monitoring system of claim 1, wherein the monitoring regulation module is further executable on the processor to calculate a first parameter-specific index for the first physiological parameter and a second parameter-specific index for the second physiological parameter, and then calculate the patient condition index based on the first and second parameter-specific indexes.

7. The patient monitoring system of claim 1, wherein the monitoring regulation module is further executable on the processor to access a first minimum measurement interval for the first wireless sensing device and a second minimum measurement interval from the second wireless sensing device, wherein the first measurement interval is not less than the first minimum measurement interval and the second measurement interval is not less than the second minimum measurement interval.

8. A method of monitoring a patient, the method comprising:
    operating a first wireless sensing device to measure a first physiological parameter from a patient and wirelessly transmit a first parameter dataset based on the first physiological parameter measurements;
    operating a second wireless sensing device to measure a second physiological parameter from the patient and wirelessly transmit a second parameter dataset based on the second physiological parameter measurements, wherein the second physiological parameter is a different physiological parameter than the first physiological parameter;
    receiving the first parameter dataset and the second parameter dataset at a receiver;
    calculating a patient condition index based on the first parameter dataset and the second parameter dataset, wherein the patient condition index is an indicator of stability of the first physiological parameter and the second physiological parameter, and wherein the patient condition index is either based equally on both the first parameter dataset and the second parameter dataset or wherein a higher weight is assigned to one of the first parameter dataset or the second parameter dataset;
    assigning, based on the patient condition index, a first measurement interval for the first physiological parameter and a second measurement interval for the second physiological parameter; and operating at least the first wireless sensing device according to the first measurement interval.

9. The method of claim 8, further comprising assigning differing weights to the first parameter dataset and the second parameter dataset, and calculating the patient condition index based further on the differing weights.

10. The method of claim 8, further comprising calculating a first parameter-specific index for the first physiological parameter based on at least the first parameter data and calculating a second parameter-specific index for the second physiological parameter based on at least the second parameter data, and calculating the patient condition index based on the first and second parameter-specific indexes.

11. The method of claim 8, further comprising operating the second wireless sensing device to measure the second physiological parameter at the second measurement interval, wherein the second measurement interval is different than the first measurement interval.

12. The method of claim 8, further comprising determining that the patient is stable based on the patient condition index, and then determining a secondary indicia of the second physiological parameter based on the first parameter dataset instead of operating the second wireless sensing device.

13. The method of claim 12, further comprising calculating the patient condition index based on the first parameter dataset and the second parameter dataset when the second wireless sensing device is operating, and determining the patient condition index based on the first parameter dataset and the secondary indicia of the second physiological parameter when the second wireless sensing device is not operating.

14. The method of claim 13, wherein the first physiological parameter is a key parameter, and wherein the patient condition index assigns higher weight to the first parameter dataset than the second parameter dataset or the secondary indicia of the second physiological parameter.

15. The method of claim 14, further comprising operating the second wireless sensing device if at least one of the first parameter dataset is not within a threshold range, the secondary indicia is not within a threshold range, and the patient condition index is not within a threshold range.

16. A method of monitoring a patient, the method comprising:

operating a first wireless sensing device to measure a first physiological parameter from a patient and wirelessly transmit a first parameter dataset based on the first physiological parameter measurements;

operating a second wireless sensing device to measure a second physiological parameter from the patient and wirelessly transmit a second parameter dataset based on the second physiological parameter measurements, wherein the second physiological parameter is a different physiological parameter than the first physiological parameter;

receiving the first parameter dataset and the second parameter dataset at a receiver;

calculating a patient condition index based on the first parameter dataset and the second parameter dataset, wherein the patient condition index is an indicator of stability of the first physiological parameter and the second physiological parameter;

determining that the patient is stable based on the patient condition index;

assigning, based on the patient condition index, a first measurement interval for the first physiological parameter;

operating at least the first wireless sensing device according to the first measurement interval; and determining a secondary indicia of the second physiological parameter based on the first parameter dataset instead of operating the second wireless sensing device.

17. The method of claim 16, further comprising calculating the patient condition index based on the first parameter dataset and the second parameter dataset when the second wireless sensing device is operating, and determining the patient condition index based on the first parameter dataset and the secondary indicia of the second physiological parameter when the second wireless sensing device is not operating.

18. The method of claim 17, wherein the first physiological parameter is a key parameter, and wherein the patient condition index assigns higher weight to the first parameter dataset than the second parameter dataset or the secondary indicia of the second physiological parameter.

* * * * *